United States Patent [19]

Oude Alink

[11] Patent Number: 4,665,180

[45] Date of Patent: May 12, 1987

[54] SUBSTITUTED TETRAHYDROPYRIMIDINES AND OCTAHYDROPHENANTHRIDINES

[75] Inventor: Bernardus A. Oude Alink, St. Louis, Mo.

[73] Assignee: Petrolite Corporation, St. Louis, Mo.

[21] Appl. No.: 779,752

[22] Filed: Sep. 25, 1985

Related U.S. Application Data

[63] Continuation-in-part of Ser. No. 668,687, Nov. 6, 1984, abandoned, which is a continuation of Ser. No. 264,899, May 18, 1981, abandoned.

[51] Int. Cl.$^4$ .................. C07D 221/12; C07D 239/70
[52] U.S. Cl. ........................................ 544/231; 546/108
[58] Field of Search ........................ 544/231; 546/108

[56] References Cited

U.S. PATENT DOCUMENTS

| | | | |
|---|---|---|---|
| 3,250,706 | 5/1966 | Kuhn et al. | 546/108 X |
| 3,536,725 | 10/1970 | Schut | 546/70 |
| 3,904,625 | 9/1975 | Oude Alink | 544/231 X |
| 3,931,191 | 1/1976 | Oude Alink | 546/283 X |
| 4,085,104 | 4/1978 | Oude Alink | 544/231 X |
| 4,113,730 | 9/1978 | Oude Alink | 544/231 X |
| 4,278,682 | 7/1981 | Szantay et al. | 546/70 X |

FOREIGN PATENT DOCUMENTS 49-26287  3/1974  Japan .................................. 544/231

OTHER PUBLICATIONS

Yun et al., Chemical Abstracts, vol. 78, 124227J, (1973).
Fieser et al., Advanced Organic Chemistry, Reinhold Publishing Co., New York, 1961, p. 478.
Carey et al., Advanced Organic Chemistry, Part B, Reactions and Synthesis, Plenum Press, New York and London (1977), pp. 24–25.

*Primary Examiner*—Donald G. Daus
*Assistant Examiner*—Diana G. Rivers
*Attorney, Agent, or Firm*—Sidney B. Ring

[57] ABSTRACT

This invention relates to certain substituted tetrahydropyrimidines and derivatives thereof, including the preparation and uses thereof.

3 Claims, No Drawings

SUBSTITUTED TETRAHYDROPYRIMIDINES AND OCTAHYDROPHENANTHRIDINES

This application is a continuation-in-part of Ser. No. 668,687 filed Nov. 6, 1984 which is a continuation application of Ser. No. 264,899 filed May 18, 1981 both now abandoned.

U.S. Pat. No. 4,085,104, Apr. 18, 1978, describes and claims substituted 2,3,4,5-tetrahydropyrimidines (THP)

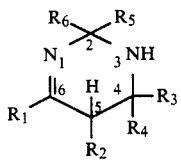

Formula I which are prepared by the following reactions:
1. The reaction of a carbonyl compound (ketone or aldehyde) with $NH_3$ or $NH_4OH$ and a sulfur-containing catalyst.
2. The reaction of an $\alpha,\beta$-unsaturated ketone and a carbonyl compound and $NH_3$ or $NH_4OH$ without a catalyst.
3. Reaction of an $\alpha,\beta$-unsaturaded ketone, a 1-aminoalcohol and $NH_3$ or $NH_4OH$ without a catalyst.

In the above formula, $R_1$, $R_2$, $R_3$, $R_4$ $R_5$ and $R_6$, which may be the same or different, are hydrogen or a hydrocarbon group such as alkyl, aryl, cycloalkyl, alkaryl, aralkyl, and substituted derivatives thereof. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, eicosyl, docosyl, for example having about 1–25 or more carbons such as from about 1–18 carbons, but preferably about 1–12 carbons. The term "alkyl" also includes isomers of the straight chain where branching occurs.

Cycloalkyl includes cyclopentyl, cyclohexyl and derivatives thereof such as alkylcyclohexyl, dialkylcyclohexyl.

Aryl, alkaryl and aralkyl include phenyl, alkylphenyl, polyalkylphenyl, chlorophenyl, alkoxyphenyl, naphthyl, alkylnapththyl, benzyl, substituted benzyl.

The joining of the R groups into a ring structure include those structures derived from reactants of the general formula

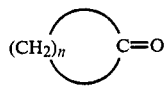

such as cyclohexanone, cyclopentanone, substituted derivatives thereof such as alkylcyclohexanone, dialkylcyclohexanone.

In U.S. Pat. No. 3,931,191 the tetrahydropyrimidines of U.S. Pat. No. 4,085,104 can be converted to substituted pyridines according to the following equation:

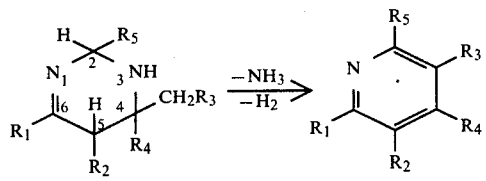

Formula II      Formula III provided the 2-position of THP contains at least 1 hydrogen and one of the groups attached to carbon 4 of THP has at least one methylene group.

The meaning of $R_1$, $R_2$, $R_3$, $R_4$, $R_5$ are the same as stated above.

The reaction is carried out by heating THP at a temperature sufficiently high to remove ammonia and hydrogen so as to cause rearrangement to the pyridine compound. In general, the temperature employed is from about 60°–400° C. or higher, such as from about 75°–350°, but preferably from about 90°–250° C., especially from about 200° to 250° C. Reduced pressure may be employed as desired so as to aid in removal of $NH_3$ and $H_2$.

The reaction can be carried out with or without a catalyst. Where a catalyst is employed it is generally of the Lewis acid type. Typical catalysts include salts, such as of inorganic or organic acids for example ammonium or amine salts of the formula

N X where N is ammonium or amine and X is an anion, for example a halide (Cl, Br, F, I), a carboxylic acid, a sulfonic acid. Other examples include ammonium acetate and ammonium benzenesulfonate, zinc halides such as zinc chloride and silica. Other catalysts include $AlCl_3$, $FeCl_3$ PbO and $Al_2O_3$.

U.S. Pat. No. 3,931,191 states that pyridines are formed in accordance with its process provided the 2-position of THP contains at least 1 hydrogen.

In U.S. Pat. No. 4,113,730 tetrahydropyrimidines containing no hydrogens in the 2-position (i.e., disubstituted in the 2-position) can be converted to octahydrophenanthridines upon deammoniation under conditions similar to U.S. Pat. No. 3,931,191.

The deammoniation is carried out in the manner of U.S. Pat. No. 3,931,191, with or without a catalyst.

The reaction of U.S. Pat. No. 3,931,191 may be summarized as follows:

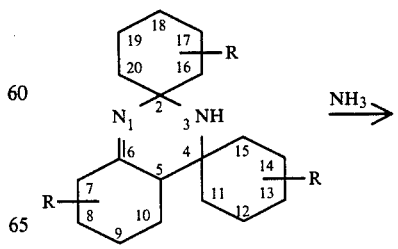

Formula IV

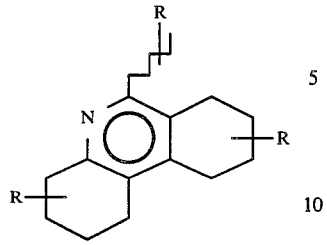

Formula V where R is hydrogen or a hydrocarbon group or substituted derivatives thereof, for example alkyl, cycloalkyl, aryl, aralkyl, alkaryl.

I have now discovered that Formula IV can be substituted in the 7-position, as the mono- or di-substituted products, by reacting it with an olefinic compound under suitable conditions. For example, the reaction is carried out between ambient temperature and 150° C. The preferred temperature range is 25°–100° C., for example 40°–90° C. A solvent may or may not be used. Time is 1 to 24 hrs.

Any olefinic compound capable of reacting with a THP in the 7-position can be employed. In general, the olefin compounds contain an activated double bond. Representative examples include olefins having the formula

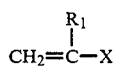

where $R_1$ is hydrogen or a hydrocarbon group, e.g. alkyl, aryl, alkaryl, aralkyl, cycloalkyl and substituted derivatives thereof as previously described, and X is a functional group, for example containing carbon, oxygen, nitrogen, sulfur, ester, nitrile, carbonyl, carboxyl, sulfur or sulfur-oxygen analogues such as dithiocarboxyl. The preferred olefinic compounds are acrylonitrile, esters of acrylic or substituted acrylic acid, for example methacrylic acid or sulfur analogs thereof such as diothioacrylic, dithioacrylates or dithiomethacrylates, or other substances having an activated double bond.

The reactions of this invention may be summarized as follows:

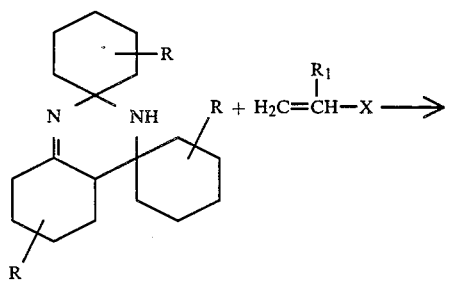

Formula IV

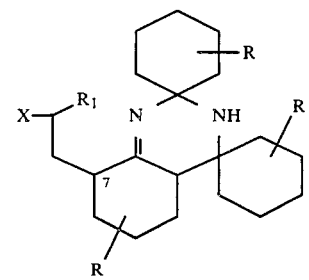

7-mono-substituted
Formula VII and

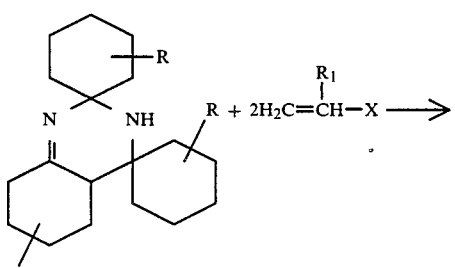

Formula IV

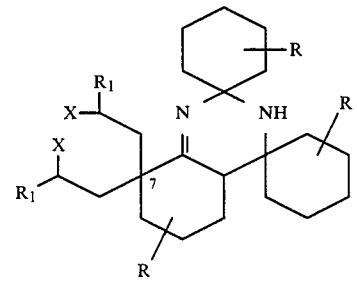

7-di-substituted
Formula VIII

The introduction of the moiety

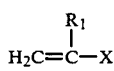

is usually stepwise with the addition of the first group being much faster than the introduction of the second group. This is believed to be due to the difference in steric hindrance between the unsubstituted and the mono-substituted THP. Therefore mono- and di-substituted THP can be isolated.

Formula VII can be converted to octahydrophenanthridines as disclosed in U.S. Pat. No. 4,113,370 to yield corresponding compounds substituted in the 7-position and which contain functional groups. The reaction is summarized as follows:

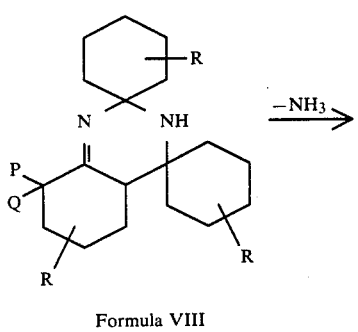

Formula VIII

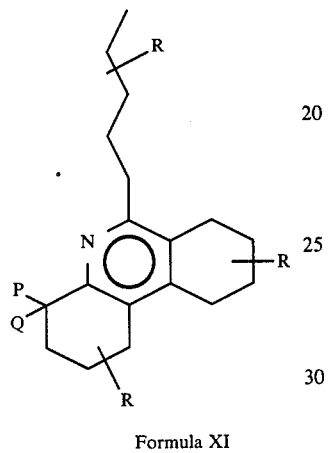

Formula XI where P is $$\text{CH}_2\overset{R_1}{\underset{|}{\text{CH}}}-X$$

as described previously, and Q is H or where both P and Q are $$\text{CH}_2\overset{R_1}{\underset{|}{\text{CH}}}-X.$$

The compositions of this invention can be converted to a wide variety of derivatives. For example, in the case of the acrylonitrile, (i.e., where $R_1$ is H and X is $C\equiv N$), the addition of acrylonitrile to THP and the subsequent conversion to an octahydrophenanthridine will yield an octahydrophenanthridine possessing a nitrile group.

As can be readily understood a great variety of different THPs can be substituted and converted to octahydrophenanthridines by this method.

The nitrile group of the compositions of this invention can be further converted to any nitrile derivative, for example, acids, imidazolines, amines or any other desired group.

In a similar fashion, for example, the addition of methyl acrylate to THP yields the methyl ester derivative of THP. Subsequent reaction with an amine will yield any derivatives of esters such as amides and trans-esterification to different esters.

The following examples are presented by way of illustration and not of limitation.

EXAMPLE 1

2,2,4,4-Dipentamethylene 5,6-tetramethylene 2,3,4,5-tetrahydropyrimidine

A mixture of 294 grams of cyclohexanone and 5 grams of ammonium chloride was placed in a pressure reactor. Over a ¾ hour period 38.8 grams of ammonia gas was added. After the addition was complexed, the mixture was stirred for 5 hours at ambient temperature. The product was taken up in toluene and the aqueous phase which separated was discarded. The toluene solution was evaporated under diminished pressure to yield 268 grams of 2,2,4,4-dipentamethylene 5,6-tetramethylene 2,3,4,5-tetrahydropyrimidine, infrared spectrum 6.02μ (C=N) and 3.05μ (N—H), $C^{13}$ nuclear magnetic resonance spectrum, solvent $CDCl_3$, ref. TMS:

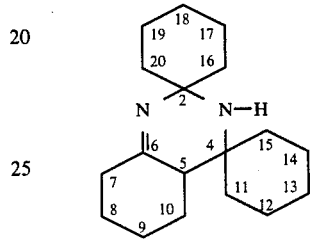

70.11(2); 50.16(4);
46.59(5); 169.38(6);
42.43(7); 29.30(8);
26.38(9); 29.30(10);
40.61(11); 21.90*(12);
26.38(13); 21.64*(14);
35.54(15); 38.53(16);
22/55*(17); 26.38(18);
22.55*(19); 38.53(20).

*values may be interchanged.

EXAMPLE 2

9,13,18-Trimethyl 2,2,4,4-dipentamethylene-5,6-tetramethylene 2,3,4,5-tetrahydropyrimidine A mixture of 75 grams of 4-methylcyclohexanone, 6.1 grams of ammonium chloride and 300 grams of toluene were placed in a pressure reactor. To the mixture was added with stirring 16.2 grams of ammonia gas over a 15 minute period. After the addition was completed, the mixture was stirred for 20 hours. The aqueous layer was removed and the toluene layer evaporated under diminished pressure to yield 66 grams of 9,13,18-trimethyl 2,2,4,4-dipentamethylene 5,6-tetramethylene 2,3,4,5-tetrahydropyrimidine, infrared spectrum 6.01μ (C=N), 3.08μ (N—H), $C^{13}$ nuclear magnetic resonance spectrum, solvent $CDCl_3$, δ in ppm.

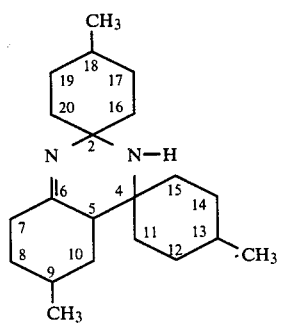

-continued 69.93(2); 49.67(4); 47.14(5);
169.60(6); 31.41(7); 34.67(8);
32.37(9); 34.67(10); 40.58(11);
29.80(12); 32.79(13); 29.80(14);
36.95(15); 37.85(16); 31.17(17);
32.79(18); 31.17(19); 37.85(20);
21.95(9-CH$_3$); 22.40(13-CH$_3$);
22.40(18-CH$_3$).

EXAMPLE 3

7-Propionitrile 2,2,4,4-Dipentamethylene 5,6-tetramethylene 2,3,4,5-tetrahydropyrimidine A mixture of 13.8 grams (0.05M) of the product described in Example 1 and 2.6 grams (0.05M) of acrylonitrile were heated at 90° C. for 18 hours. Evaporation under diminished pressure yielded 16.2 grams of product. $^{13}$C nmr spectrum, solvent CDCl$_3$, ref. TMS, δ in ppm.

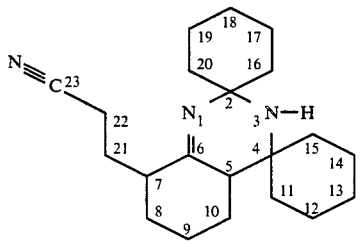

70.0(2,s); 50.0(4,s); 46.5(5,d);
168.0(6,s); 47.0(7,d); 36.4(8);
26.1(9); 37.0(10); 43.0(11);
21.4(12); 26.1(13); 22.0(14);
41.2(15); 38.6(16); 22.9(17);
26.1(18); 22.9(19); 39.4(20);
29.5(21); 14.8(22); 120.1(23,s).

s = singlet,
d = doublet determined by allowing C—H coupling

EXAMPLE 4

7,7-Dipropionitrile 2,2,4,4-Dipentamethylene 5,6-tetramethylene 2,3,4,5-tetrahydropyrimidine A mixture of 1.8 grams (0.0066M) of the product described in example 1 and 6.5 grams (0.12M) of acrylonitrile was refluxed for 19 hours. Evaporation under diminished pressure yielded dicyanoethylated 2,2,4,4-dipentamethylene 5,6-tetramethylene 2,3,4,5-tetrahydropyrimidine. $^{13}$C nmr, solvent CDCl$_3$, ref. TMS. δ in ppm:

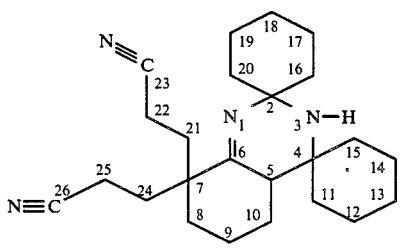

70.1(2,s); 50.4(4,s); 42.2(5,d);
166.7(6,s); 45.3(7,s); 33.9(8);
26.8(9); 35.6(10); 40.9(11);
20.5(12); 26.0(13); 21.2(14);
41.6(15); 40.5(16); 22.6(17);
26.0(18); 22.6(19); 38.4(20);

-continued 27.4(21); 12.1(22); 120.4(23,s);
31.3(24); 11.6(25); 119.6(26,s).

s = singlet,
d = doublet determined by allowing C—H coupling

EXAMPLE 5

7-(Methylpropionate)-2,2,4,4-Dipentamethyl 5,6-tetramethylene 2,3,4,5-tetrahydropyrimidine A sample of 27.4 grams of the product described in example 1 and 8.6 grams of methyl acrylate were heated for 18 hrs. at 50° C. The resulting product was evaporated under diminished pressure to yield 35.9 grams of the substituted tetrahydropyrimidine: $^{13}$C nmr, solvent CDCl$_3$, ref. TMS δ in ppm.

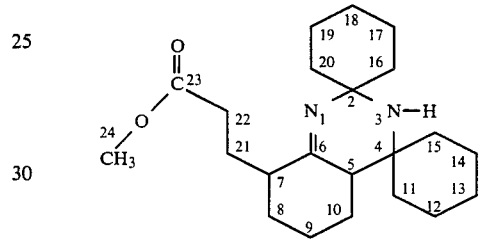

70.0(2); 51.0(4); 48.2(5);
168.6(6); 46.6(7); 36.5(8);
26.2(9); 37.3(10); 43.1(11);
21.6(12); 26.2(13); 22.1(14);
41.2(15); 38.6(16); 22.9(17);
26.2(18); 22.9(19); 39.5(20);
29.7(21); 31.8(22); 174.4(23);
50.1(24).

In summary, this invention relates to 7-mono and di-substituted compounds of the formula

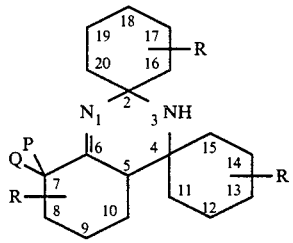

where R is hydrogen or a hydrocarbon group as previously described and where at least one of P and Q is an alkyl group having an ester, nitrile, carboxyl or dithiocarboxyl group attached thereto (if only one of the 7-position is substituted, the other position is H).

These THPs can be converted to the corresponding octahydropyrimidines as follows:

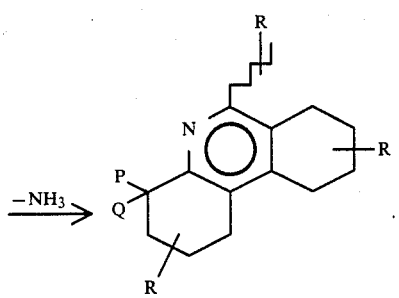

The 7-monosubstituted compounds can be converted to the corresponding phenanthridines as follows:

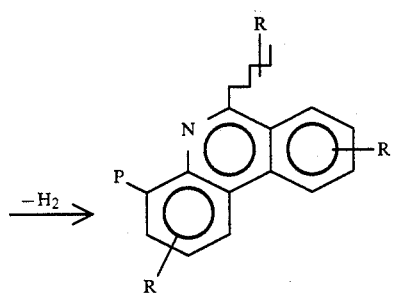

This invention also relates to the preparation of these 7-substituted compositions by reacting THP with an activated olefin which can be converted to octahydrodrophenanthridines by deammoniation and to phenanthridines by dehydrogenation. The functional group on P and/or Q can be converted to any derivatives of the functional group thereon.

The compositions of this invention have a wide variety of uses. They are particularly useful as corrosion inhibitors, particularly in deep oil and gas wells.

I claim:

1. Compounds of the formula

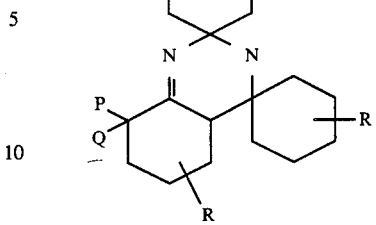

wherein R is hydrogen or a hydrocarbon group; P is an ethylene group having an ester, nitrile, carboxyl or thiocarboxyl group attached to the beta carbon thereof; and Q is a hydrogen or an ethylene group having an ester, nitrile, carboxyl or thiocarboxyl group attached to the beta carbon thereof.

2. Compounds of the formula

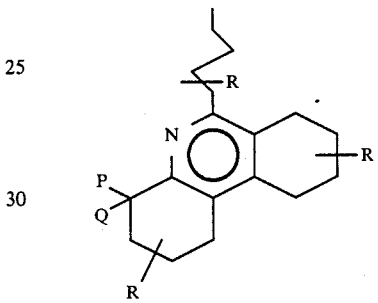

wherein R is hydrogen or a hydrocarbon group; P is an ethylene group having an ester, nitrile, carboxyl or thiocarboxyl group attached to the beta carbon thereof; and Q is hydrogen or an ethylene group having an ester, nitrile, carboxyl or thiocarboxyl group attached to the beta carbon thereof.

3. Compounds of the formula

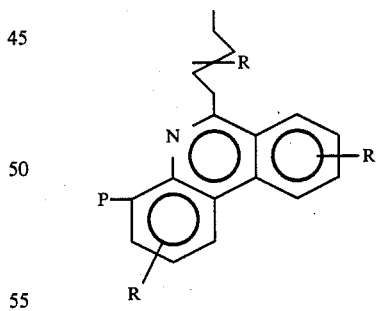

wherein R is hydrogen or a hydrocarbon group and P is an ethylene group containing an ester, nitrile, carboxyl or thiocarboxyl group attached to the beta carbon thereof.

* * * * *